United States Patent
Santucci (10) Patent No.: US 10,829,459 B2
(45) Date of Patent: Nov. 10, 2020

(54) LOW-ENERGY CONSUMPTION PROCESS WITH REDUCED AMMONIA CONSUMPTION, FOR THE PRODUCTION OF HIGH-PURITY MELAMINE THROUGH THE PYROLYSIS OF UREA, AND RELATIVE PLANT

(71) Applicant: EUROTECNICA MELAMINE, LUXEMBURG, ZWEIGNIEDERLASSUNG IN ITTIGEN, Ittigen (CH)

(72) Inventor: Roberto Santucci, Gorla Maggiore (IT)

(73) Assignee: EUROTECNICA MELAMINE, LUXEMBURG, ZWEIGNIEDERLASSUNG IN ITTIGEN, Ittigen (CH)

( * ) Notice: Subject to any disclaimer, the term of this patent is extended or adjusted under 35 U.S.C. 154(b) by 0 days.

(21) Appl. No.: 16/458,343

(22) Filed: Jul. 1, 2019

(65) Prior Publication Data
US 2020/0024242 A1    Jan. 23, 2020

(30) Foreign Application Priority Data

Jul. 20, 2018    (IT) .................. 102018000007367

(51) Int. Cl.
*C07D 251/60*    (2006.01)
*C07D 251/62*    (2006.01)

(52) U.S. Cl.
CPC ......... *C07D 251/60* (2013.01); *C07D 251/62* (2013.01)

(58) Field of Classification Search
CPC ............................ C07D 251/60; C07D 251/62
USPC .................................................. 544/201, 203
See application file for complete search history.

(56) References Cited

U.S. PATENT DOCUMENTS

2011/0275806 A1* 11/2011 Borrini ................ C07D 251/62
544/201

FOREIGN PATENT DOCUMENTS

| DE | 102016112944 A1 | 1/2017 |
| EP | 2385043 A1 | 11/2011 |
| WO | 02100839 A1 | 12/2002 |

OTHER PUBLICATIONS

Fanni, Stefano, "Italian Search Report and Written Opinion for Italian Application No. IT201800007367," Italian Patent and Trademark Office, dated Mar. 15, 2019.

* cited by examiner

*Primary Examiner* — Venkataraman Balasubramanian
(74) *Attorney, Agent, or Firm* — Florek & Endres PLLC (57) ABSTRACT

A process is described, having a low-energy consumption and reduced ammonia consumption for the production of high-purity melamine, through the pyrolysis of urea, and the relative plant.

19 Claims, 4 Drawing Sheets

LOW-ENERGY CONSUMPTION PROCESS WITH REDUCED AMMONIA CONSUMPTION, FOR THE PRODUCTION OF HIGH-PURITY MELAMINE THROUGH THE PYROLYSIS OF UREA, AND RELATIVE PLANT

FIELD OF THE INVENTION

The present invention relates to a low-energy consumption process with reduced ammonia consumption for the preparation of high-purity melamine through the pyrolysis of urea and the relative plant.

BACKGROUND OF THE INVENTION

To better understand the object of the present invention, reference is made to the state of the art as described hereunder. It is known that the transformation of molten urea into melamine is described by the following overall reaction (1):

$$6NH_2CONH_2 \rightarrow (CN)_3(NH_2)_3 + 6NH_3 + 3CO_2 \qquad (1)$$

urea melamine ammonia carbon dioxide
wherein 1.86 kg of $NH_3$ and $CO_2$, as a whole called off-gases, are formed for each kg of melamine.

A particularly widespread industrial process, based on the high-pressure pyrolysis of urea, is described in patent EP2385043. In order to clearly appreciate the improvements and advantages of the process according to the present invention, FIG. 1 of the present patent application is representative of the state of the art and shows a simplified block-diagram of an embodiment of the production process of melamine described in EP2385043.

Figure 1:
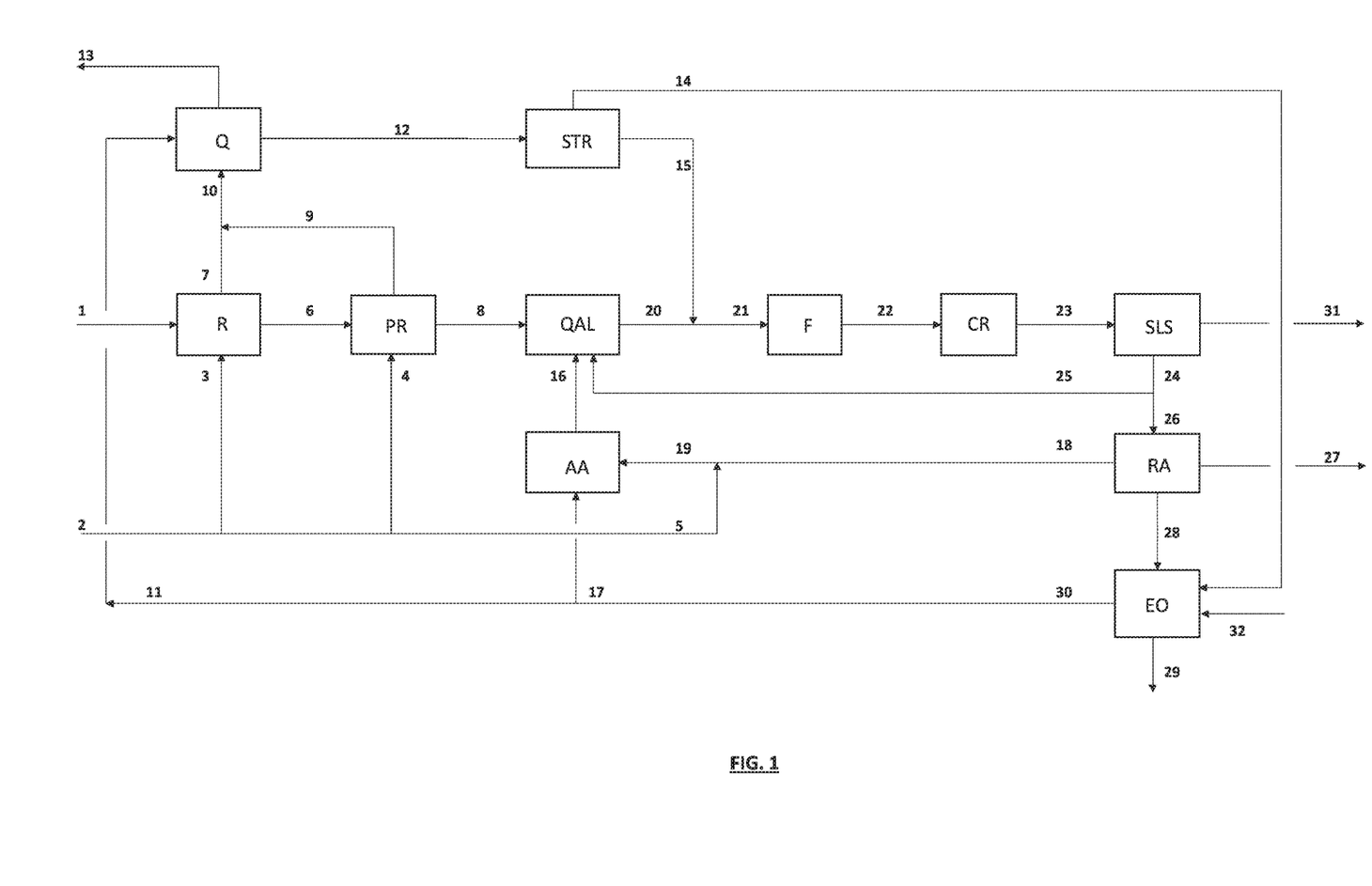
FIG. 1 is a block diagram of the process of EP2385043.

According to the scheme of FIG. 1, the process of EP2385043 comprises the following steps:
  a) producing melamine by the pyrolysis of urea in a specific reactor and separating a biphasic liquid/gas effluent produced in the pyrolysis reaction of urea into a liquid stream of raw melamine and into a first stream of anhydrous off-gases comprising $NH_3$, $CO_2$ and melamine vapour;
  b) putting the above-mentioned liquid stream of raw melamine in contact with a stream of anhydrous gaseous $NH_3$ in a specific post-reactor, forming a liquid stream of raw melamine impoverished in $CO_2$ and a second stream of anhydrous off-gases comprising $NH_3$, $CO_2$ and melamine vapour;
  c) putting said first and second stream of anhydrous off-gases in contact with at least one aqueous washing stream to form an aqueous stream comprising melamine, $NH_3$ and $CO_2$ and a stream of wet off-gases comprising $NH_3$, $CO_2$ and water vapour:
  d) removing from said aqueous stream comprising melamine, $NH_3$ and $CO_2$, at least a part of the $CO_2$ contained therein, forming a stream comprising the $CO_2$ removed and an aqueous stream comprising melamine impoverished in $CO_2$;
  e) recovering the melamine contained in said liquid stream of raw melamine impoverished in $CO_2$ and the melamine contained in said aqueous stream comprising melamine impoverished in $CO_2$ through crystallization by cooling and separation, with the formation of a stream of crystallized melamine and a stream of mother liquor.

The block diagram of FIG. 1 shows the main sections of a plant for the production of melamine and the main streams of materials, according to the process of EP2385043, represented at the inlet by the stream of liquid urea (stream 1), the stream of liquid ammonia (stream 2) and the stream of make-up water (stream 32) and the outgoing streams represented by the stream of off-gases (stream 13), the stream of melamine produced (stream 31), the stream of carbonate (stream 27) and the stream of purified water (stream 29) if not reused within the plant.

The stream 1 of liquid urea is fed to the reaction section R, at a temperature higher than the melting temperature (equal to about 133° C.) and the stream 3 of anhydrous gaseous $NH_3$. The section R comprises a reactor equipped with a suitable heating system which keeps the reagent system at a temperature of about 360-420° C.; the pressure is maintained at a value higher than 70 $bar_{rel}$.

The liquid/gas biphasic effluent produced by the pyrolysis reaction of urea, is separated, inside the reactor R, or in one or more separators positioned downstream (not shown in FIG. 1), into a liquid stream 6 of raw melamine comprising unreacted urea, $NH_3$, $CO_2$ and impurities such as OATs and polycondensates, and a first stream of anhydrous off-gases 7 comprising $NH_3$, $CO_2$ saturated with melamine vapour. The liquid stream 6 of raw melamine and the stream 7 of anhydrous off-gases are subjected to two different treatments for the recovery of melamine contained therein.

The liquid stream 6 of raw melamine is sent to a post-reaction section PR, which preferably operates under the same temperature and pressure conditions as the section R, wherein the same is put in contact with a stream of anhydrous gaseous $NH_3$. The mass ratio between said stream 4 and said stream 6 can vary from 0.06 to 0.6. The stream of anhydrous gaseous $NH_3$ flows in close contact with the liquid stream of raw melamine and extracts the $CO_2$ dissolved therein, increasing the partial pressure of ammonia. Furthermore, the permanence of raw melamine under the post-reactor conditions has some advantageous secondary effects:
  a) it almost completely advances the conversion of the unreacted urea into melamine, resulting in an increase in the yield and reducing, in the sections downstream, the formation of $CO_2$ due to a possible decomposition of residual urea;
  b) it advances the conversion of OATs into melamine. The conversion degree of OATs into melamine is a function of the residence time of the stream 6 in contact with the stream 4 in the PR section;
  c) increasing the partial pressure of $NH_3$, it favours the reconversion of the polycondensates into melamine, lowering the concentration by over 20%.

From the above, it is clear that the greater the amount of ammonia that is fed to the post-reactor, the greater the effect of the $CO_2$ removal and the greater the partial pressure of the ammonia in liquid phase inside the post-reactor, will be. It is also clear, however, that the greater the amount of $NH_3$, the greater will be the melamine coming out in vapour phase with the stream 9 and that will have to be absorbed and solubilized in the following section Q, and the quantity of wet off-gases to be sent to the urea plant.

Consequently, in fact, in the process according to EP238504, in order to reduce the amount of off-gas, there is the tendency to send the smallest possible amount of ammonia to the Post-Reactor which is necessary for a satisfactory but still not complete transformation of the by-products.

A liquid stream of partially purified melamine (stream 8) therefore exits from the PR section, having a low $CO_2$ content, with a low content of unreacted urea and reduced quantities of OATs and polycondensates. A second stream of anhydrous off-gases (stream 9) also exits from the PR section, mainly comprising $NH_3$, a small amount of $CO_2$ and a certain quantity of melamine vapour. The streams of anhydrous off-gases coming from the sections R and PR, joined in a single stream 10, are subjected to a recovery treatment of the melamine by washing with water, in a single washing section Q. The stream 10 can contain melamine vapour up to 10% by mass of the overall melamine produced in the section R. In the section Q this melamine is recovered by putting the stream 10 in contact with an aqueous washing stream, preferably consisting of one or more streams collected from suitable points of the melamine plant (in FIG. 1, these streams are represented by a single stream 11), with the formation of an aqueous stream (stream 12) comprising melamine, $NH_3$ and $CO_2$. The section Q operates at temperatures within the range of 125–190° C. and pressures within the range of 20-30 $bar_{rel}$; the mass ratio between the stream 11 and the stream 10 ranges from 0.3 to 2.0.

The gaseous stream leaving the section Q after the washing (stream 13), consists of wet off-gases substantially comprising $NH_3$, $CO_2$ and the saturation water vapour; it is sent to the urea plant as such or after being subjected to treatment (not shown in FIG. 1), such as, for example, condensation by absorption in aqueous solution. There is therefore a wet stream of off-gases consisting of $NH_3+CO_2+H_2O$ which is sent to the urea plant with negative effects due to the presence of water.

The aqueous stream leaving the section Q (stream 12) is sent to a $CO_2$ separation section STR, where a part of the $CO_2$ contained therein is removed by means of stripping with vapour, produced for example by a reboiler at the bottom of the same stripper. A gaseous stream rich in $CO_2$ (stream 14), which is sent to a point of the process in which it can no longer contribute to lowering the pH in the crystallization, and an aqueous stream comprising melamine impoverished in $CO_2$ (stream 15), are recovered from the section STR.

As already mentioned, the liquid stream of melamine 8, substantially free of $CO_2$, also exits from the post-reaction section PR. It is sent to a quench-ammonolysis section QAL, where the quench treatment (dissolution in water of the raw melamine) and ammonolysis (elimination of the polycondensates) are effected.

The section QAL can be composed of one or more stationary apparatuses, preferably a single apparatus. The stream 8 enters the bottom of this equipment, kept under vigorous stirring, and is put in close contact with an aqueous ammonia solution (stream 16), in which the same is totally dissolved at a temperature of 160-180° C. The aqueous stream 16 is formed by the combination of an aqueous stream (stream 17) coming from the subsequent steps of the melamine process, and a stream of $NH_3$ (stream 19) formed, in turn, by the combination of the stream of $NH_3$ (stream 18) also coming from the subsequent steps of the melamine process and the make-up stream of $NH_3$ 5; a direct recycling aqueous stream of the crystallization mother liquor (stream 25) is also sent to the quench-ammonolysis section.

At the inlet of the quench-ammonolysis section, the mass ratios between the combination of streams 16 and 25 and the stream of molten melamine 8, are selected so as to have mass concentrations of $NH_3$ at the outlet ranging from 10% to 17% in the aqueous ammonia solution comprising purified melamine (stream 20).

In the quench-ammonolysis equipment, the residence time is sufficient for almost completely eliminating the polycondensates present in the stream 8, mainly transforming the same into melamine.

The stream 15 coming from the section STR is preferably joined with stream 20 leaving the quench-ammonolysis section to form the stream 21; from this point, the melamine leaving the reaction section R and post-reaction section PR in vapour phase, is joined with the melamine that has left the same sections in liquid phase, and is subjected to the same treatment.

The stream 21 is sent to the filtration section F, composed of finisher filters which also complete the ammonolysis treatment. The stream leaving the section F (stream 22) is sent to the crystallization section Cr, where the melamine is crystallized by decreasing the temperature to a value of about 40-50° C., obtaining an aqueous suspension of high-purity melamine (stream 23).

The low content of $CO_2$ in stream 15, obtained by means of the section STR and the low content of $CO_2$ in stream 8 obtained through the section PR, allow the pH to be kept high in crystallization, thus operating under less favourable conditions for the precipitation of OATs. These advantageous conditions for the crystallization of pure melamine are obtained in the section STR, by separating the $CO_2$ from the melamine stream recovered from the off-gases (stream 12) and in the section PR, by stripping the $CO_2$ with $NH_3$ leaving the urea plant (stream 4) and is returned to the same together with the wet off-gases (stream 13).

The stream 23 leaving the section Cr is subjected to a solid/liquid separation in the section SLS, where the melamine crystals (stream 31) are separated from the crystallization mother liquor (stream 24) and sent to the drying and packaging sections (not shown in FIG. 1).

The stream 24 leaving the separator SLS is divided into two streams (stream 25 and 26): the stream 25 is recycled directly to the quench-ammonolysis section QAL, whereas the stream 26 is sent to the ammonia recovery section RA.

The fraction of mother liquor not directly recycled (stream 26) is subjected to deammoniation in the section RA, which separates three streams: a stream of $NH_3$ substantially free of $CO_2$, to be recycled to the ammonolysis section QAL (stream 18); a stream rich in $CO_2$ and ammonia (stream 27); an aqueous stream comprising melamine, OATs and substantially free of $CO_2$ and $NH_3$ (stream 28).

The stream of $NH_3$ 18 is extracted from the section RA, preferably in the gaseous state and then mixed, after joining with the ammonia make-up stream 5, with the aqueous stream 17, coming from the subsequent phases of the melamine process, in the ammonia absorption section (AA); in this way, the condensation enthalpy of $NH_3$ heats the resulting stream 16, with a positive effect on the thermal balance of the section QAL and therefore on the vapour consumption of the whole plant. The stream 27 containing $CO_2$, ammonia and water, normally called side stream, is sent directly to the urea plant, thus eliminating $CO_2$ from the plant, but also eliminating the ammonia contained in the solution forming stream 27. This ammonia must be reintegrated by means of make-up or reintegration (stream 5). The melamine plant therefore requires a total quantity of ammonia equal to the sum of streams 3-4-5 (stream 2).

The stream of deammoniated mother liquor 28 is sent to a section EO for elimination of the OATs and to obtain an aqueous solution (stream 30) to be recycled to the quench-ammonolysis section QAL (stream 17) and off-gas washing section Q (stream 11).

The section EO can be implemented in many different ways. In EP2385043, the whole stream 28 is sent for decomposition in order to recover the organic compounds in the form of $NH_3$ and $CO_2$, obtaining a stream of water (stream 29) substantially free of impurities, which can be discharged or re-used in a suitable point of the plant, and a stream of water 30 to be recycled to the sections QAL and Q (streams 17 and 11). The section EO also receives the make-up water (stream 32) in order to reintegrate the exits of water with the off-gases (stream 13), side stream (stream 27) and with the stream 29 if discharged and not recycled to the plant.

The process and plant according to the prior art, more specifically according to EP2385043, have been further improved, however, obtaining, in a completely surprising way, a process and plant which, maintaining all the advantages previously described, are more efficient in terms of reduction of the need for fresh ammonia from the battery limits, energy consumptions and the quantity of wet off-gases at the outlet which must be reconverted to urea.

As previously pointed out, in fact, in the process according to EP2385043, the melamine that exits in vapour phase with the stream 9, is absorbed and solubilized in the section Q, therefore the greater the quantity of anhydrous gases in stream 9, the greater the quantity of wet off-gases produced in Q which must be treated and reconverted to urea in the urea production plant, and the greater the quantity of water necessary for solubilizing the melamine contained therein.

Furthermore, as the solution containing melamine (stream 12) is fed to a stripping section STR, another drawback linked to the quantity of ammonia fed to the post-reactor is therefore represented by the amount of vapour necessary for carrying out the stripping of $CO_2$.

In order to reduce as much as possible the drawbacks linked to the amount of ammonia fed to the post-reactor indicated above, in the processes according to the state of the art, there is consequently the tendency to feed the minimum possible amount of ammonia necessary for reaching a satisfactory degree of transformation of the by-products, but not sufficient, however, for guaranteeing the complete transformation of the same.

SUMMARY OF THE INVENTION

The objective of the present invention is therefore to provide a process and plant which overcome the drawbacks of the state of the art described above and which are characterized by a reduced consumption of ammonia, an improved efficiency and, at the same time, with reduced production costs of melamine.

An object of the present invention therefore relates to a process for the production of melamine by the pyrolysis of urea which comprises the following steps:
a) producing melamine by the pyrolysis of urea in a specific reactor and separating a biphasic liquid/gas effluent produced in the pyrolysis reaction of urea into a liquid stream of raw melamine and into a first stream of anhydrous off-gases comprising $NH_3$, $CO_2$ and melamine vapour;
b) putting said liquid stream of raw melamine in contact with a stream of anhydrous gaseous $NH_3$ in a specific post-reactor and forming a liquid stream of melamine impoverished in $CO_2$ and partially purified and a second stream of anhydrous gas comprising $NH_3$, $CO_2$ and melamine vapour;
c) putting the first stream of anhydrous gas coming from step a) in contact with at least one aqueous washing stream, forming an aqueous stream, comprising melamine, $NH_3$, $CO_2$ and a gaseous stream of wet off-gases comprising $NH_3$, $CO_2$ and water vapour;
d) mixing the second stream of anhydrous gases coming from step b) with a stream of recycled water and forming an aqueous ammonia solution in which the melamine contained in the stream of anhydrous gases is dissolved, recovering the sensible heat and condensation heat of the gases;
e) removing, from the aqueous stream of step c), comprising melamine, $NH_3$, $CO_2$, at least a part of the $CO_2$ contained therein and forming a gaseous stream comprising the $CO_2$ removed and an aqueous stream comprising melamine, $NH_3$ and impoverished in $CO_2$;
f) subjecting the liquid stream of melamine impoverished in $CO_2$ and partially purified, leaving the post-reactor, to a quench-ammonolysis treatment by contact with the aqueous ammonia solution obtained in step d), and the formation of an aqueous ammonia stream comprising purified melamine;
g) recovering the melamine contained in the aqueous ammonia stream comprising purified melamine coming from step f) and the melamine contained in said aqueous stream comprising melamine and impoverished in $CO_2$ coming from step (e) by means of a crystallization step by cooling and separation, with the formation of a stream of crystallized melamine and a stream of mother liquor.

A second object of the present invention relates to a plant for the application of the above-mentioned process, comprising:
i) a separation section for separating a biphasic liquid/gas effluent produced in a pyrolysis reaction of urea into a liquid stream of raw melamine and a first stream of anhydrous off-gases comprising $NH_3$, $CO_2$ and melamine vapour, said separation section being connected to a reaction section for the pyrolysis of urea from which it receives said biphasic liquid/gas effluent, said separation section being inside or outside said reaction section;
ii) a stripping section or post-reactor for putting said liquid stream of raw melamine coming from said reaction section in contact with a stream of anhydrous gaseous $NH_3$ and forming a liquid stream of melamine impoverished in $CO_2$ and partially purified and a second stream of anhydrous gases comprising $NH_3$, $CO_2$ and melamine vapour, said stripping section being connected to said reaction section from which it receives said liquid stream of raw melamine;
iii) a washing section for putting said first stream of anhydrous off-gases in contact with an aqueous washing stream and forming an aqueous stream comprising melamine, $NH_3$, $CO_2$ and a stream of wet off-gases comprising $NH_3$, $CO_2$ and water vapour, said washing section being connected to said separation section from which it receives said first stream of anhydrous off-gases;
iv) a removal section of the $CO_2$ for removing from said aqueous stream comprising melamine, $NH_3$, $CO_2$, at least a part of the $CO_2$ contained therein and comprising the $CO_2$ removed and an aqueous stream, comprising melamine, $NH_3$ and impoverished in $CO_2$, said removal section of the $CO_2$ being connected to said washing section from which it receives said aqueous stream, comprising melamine, $NH_3$ and $CO_2$;
v) a mixing and heat recovery section for mixing said second stream of anhydrous gases with a stream of recycled water and forming an aqueous ammonia solution in which the melamine contained in the stream of anhydrous off-gases is dissolved, and for recovering both the sensible heat and the condensation heat of the gases, by absorption of the ammonia, said mixing and heat recovery section being connected to the stripping section or post-reactor from which it receives said second stream of anhydrous gases and said quench-ammonolysis section to which the aqueous ammonia solution is fed;
vi) a quench-ammonolysis section for subjecting the liquid stream of melamine impoverished in $CO_2$ and partially purified, leaving the post-reactor, to a quench-ammonolysis treatment by contact with the aqueous ammonia solution coming from the mixing and heat recovery section, and forming an aqueous ammonia stream, comprising purified melamine, said quench-ammonolysis section being connected to said stripping section or post-reactor from which it receives said liquid stream of melamine impoverished in $CO_2$ and partially purified;

vii) at least one recovery section of the melamine for recovering both the melamine contained in said aqueous ammonia stream comprising purified melamine and also the melamine contained in said aqueous stream comprising melamine, $NH_3$ and impoverished in $CO_2$ through crystallization by cooling and separation, with the formation of a stream of crystallized melamine and a stream of mother liquor, said recovery section of the melamine being connected to both said quench-ammonolysis section from which it receives the aqueous ammonia stream comprising purified melamine and to said removal section of the $CO_2$ from which it receives said aqueous stream comprising melamine, $NH_3$ and impoverished in $CO_2$.

In its essence, the process object of the present invention provides for the collection and purification in aqueous solution of the melamine produced in the pyrolysis reactor and its separation by crystallization. More specifically, the invention relates to the recovery of the gases leaving the post-reactor within the process for the production of melamine. Even more specifically, the gases leaving the post-reactor are absorbed and condensed in recycled water, recovering the melamine contained therein, thus obtaining the ammonia solution necessary for the purification of melamine and, at the same time, recovering both the sensible heat and the condensation heat of the ammonia.

More specifically, the process according to the present invention, by sending the gases leaving the post-reaction section to the mixing and heat recovery section, i.e. to the ammonia absorption section, and no longer to the off-gas washing section, overcomes the drawbacks of the state of the art, i.e. the fact of having to run with the minimum possible flow-rate of ammonia to the post-reactor to reduce the off-gases and consequently not completing the transformation of the by-products.

BRIEF DESCRIPTION OF THE DRAWINGS

The present invention will be better understood when considered in view of the attached drawings. The drawings, however, are presented merely to illustrate the invention without limiting the invention in any manner whatsoever.

DETAILED DESCRIPTION OF THE PREFERRED EMBODIMENT

The process according to the present invention is therefore characterized by the recovery of the anhydrous off-gases leaving the post-reactor and by their condensation by mixing with recycled water, also guaranteeing an optimization of the use of make-up ammonia and a reduction in the total water leaving the plant, both that contained in the off-gases and also that contained in the solution to be treated in the urea plant, with the contemporaneous recovery within the melamine plant, of the discharge water, thus implementing a process without liquid discharges towards the outside.

In the present description, "washing aqueous stream", unless otherwise specified, refers to a stream of make-up water or it can consist of one or more aqueous streams taken from suitable points of the melamine plant itself.

In the present description, "aqueous stream comprising melamine and impoverished in $CO_2$" refers to a stream leaving a step of the process with a lower $CO_2$ content with respect to the stream fed to said process step, whereas "liquid stream of melamine impoverished in $CO_2$ and partially purified" refers to a stream leaving a step of the process with a lower content of $CO_2$ and impurities with respect to the stream fed to said process step.

In step d) of the process according to the present invention, the second stream of anhydrous gases coming from step b) is preferably mixed with the stream of recycled water and with a stream obtained by combining a stream of make-up ammonia and a stream of recycled ammonia to form said aqueous ammonia solution.

The process according to the present invention can comprise feeding the make-up ammonia stream to a subsequent deammoniation treatment of the portion of the stream of mother liquor not directly recycled.

At least a part of said stream of mother liquor obtained in step g) can be preferably used as aqueous stream in step f) for the quench-ammonolysis treatment of said liquid stream of melamine impoverished in $CO_2$ and partially purified, leaving the post-reactor, and at least a part of said stream of mother liquor obtained in step g) can be subjected to deammoniation treatment with the formation of a gaseous stream of $NH_3$ substantially free of $CO_2$, a stream comprising $CO_2$, ammonia and water and an aqueous stream of deammoniated mother liquor.

Said stream comprising $CO_2$, ammonia and water, coming from the deammoniation treatment, can be joined with a further stream, containing $H_2O$, $CO_2$ and $NH_3$ coming from a subsequent decomposition step carried out on said aqueous stream of deammoniated mother liquor, to form a single stream to be recycled to a plant for the production of urea either directly or after treatment which reduces the water content, or said stream containing $CO_2$, ammonia and water is sent to the washing step (c) of the anhydrous off-gases.

The aqueous stream of deammoniated mother liquor can be subjected to a decomposition treatment with the recovery of $NH_3$ and $CO_2$ and the production of an aqueous stream which is partially recycled as aqueous washing stream to said step c) and partially recycled as aqueous stream to contribute to forming the aqueous ammonia stream (step d)) fed to the quench-ammonolysis treatment (step 1)) and a stream containing $H_2O$, $CO_2$ and $NH_3$ which is combined with the stream comprising $CO_2$, ammonia and water coming from the deammoniation treatment.

The gaseous stream of $NH_3$, substantially free of $CO_2$, coming from the deammoniation treatment, can be mixed with a part of said aqueous stream in order to recover the condensation heat in step d).

The aqueous stream comprising melamine, coming from step e), can be joined with said aqueous ammonia stream comprising purified melamine coming from the quench-ammonolysis step f), with the formation of a single stream to be subjected to said step g).

In step e) the removal of $CO_2$ from the aqueous stream comprising melamine, $NH_3$ and $CO_2$, is effected by means of depressurization or by stripping. The stream comprising the removed $CO_2$ obtained in step e), is recycled to a step of the same process subsequent to said recovery step g) for the recovery of melamine through crystallization by cooling.

The stream of wet off-gases comprising $NH_3$, $CO_2$ and water vapour obtained in step c) is preferably recycled to a plant for the production of urea, as such or after being subjected to a condensation treatment by absorption in aqueous solution or another type of treatment.

Figure 2:
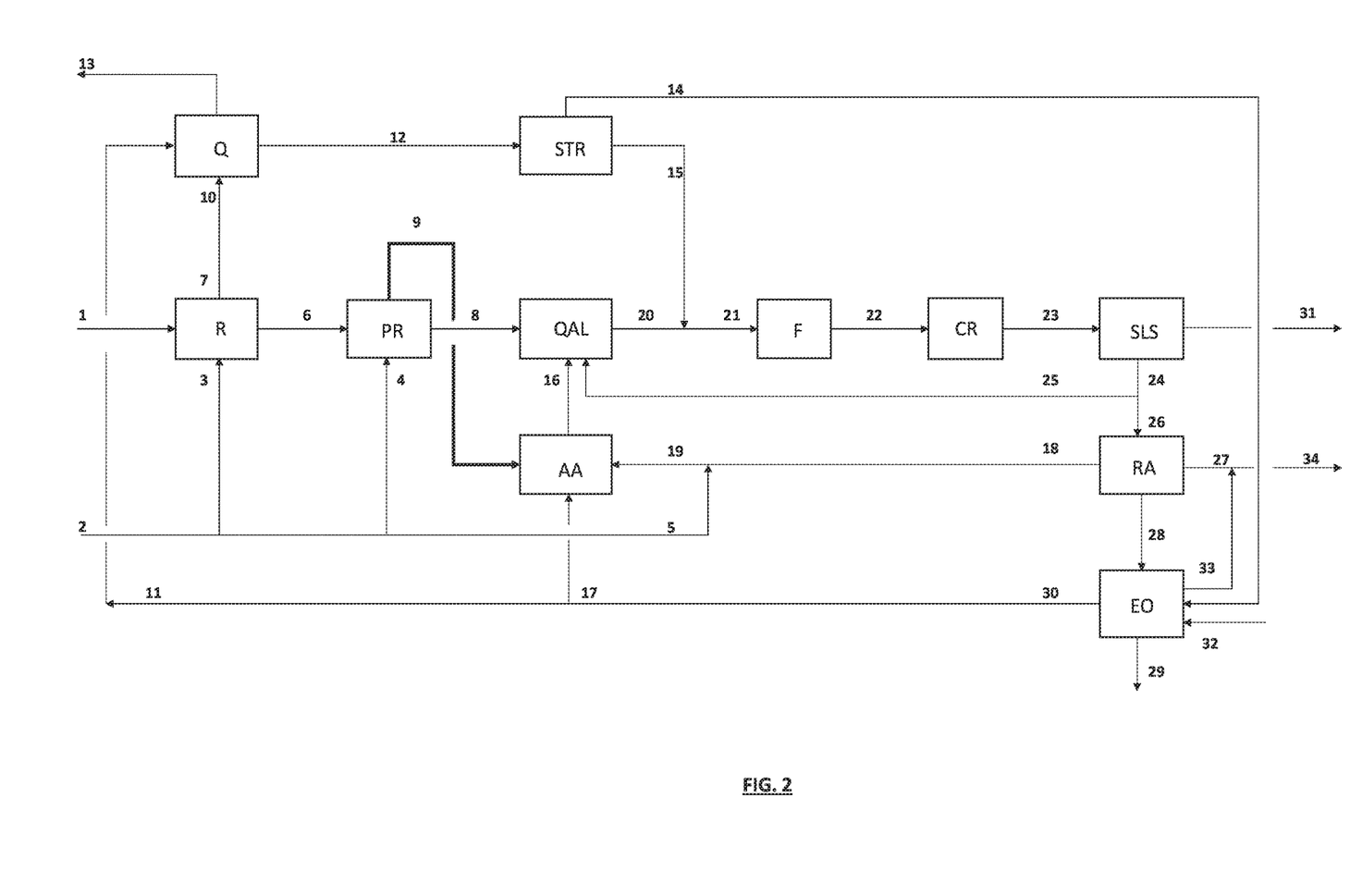
FIG. 2 is a block diagram of an embodiment of the present invention.
Figure 3:
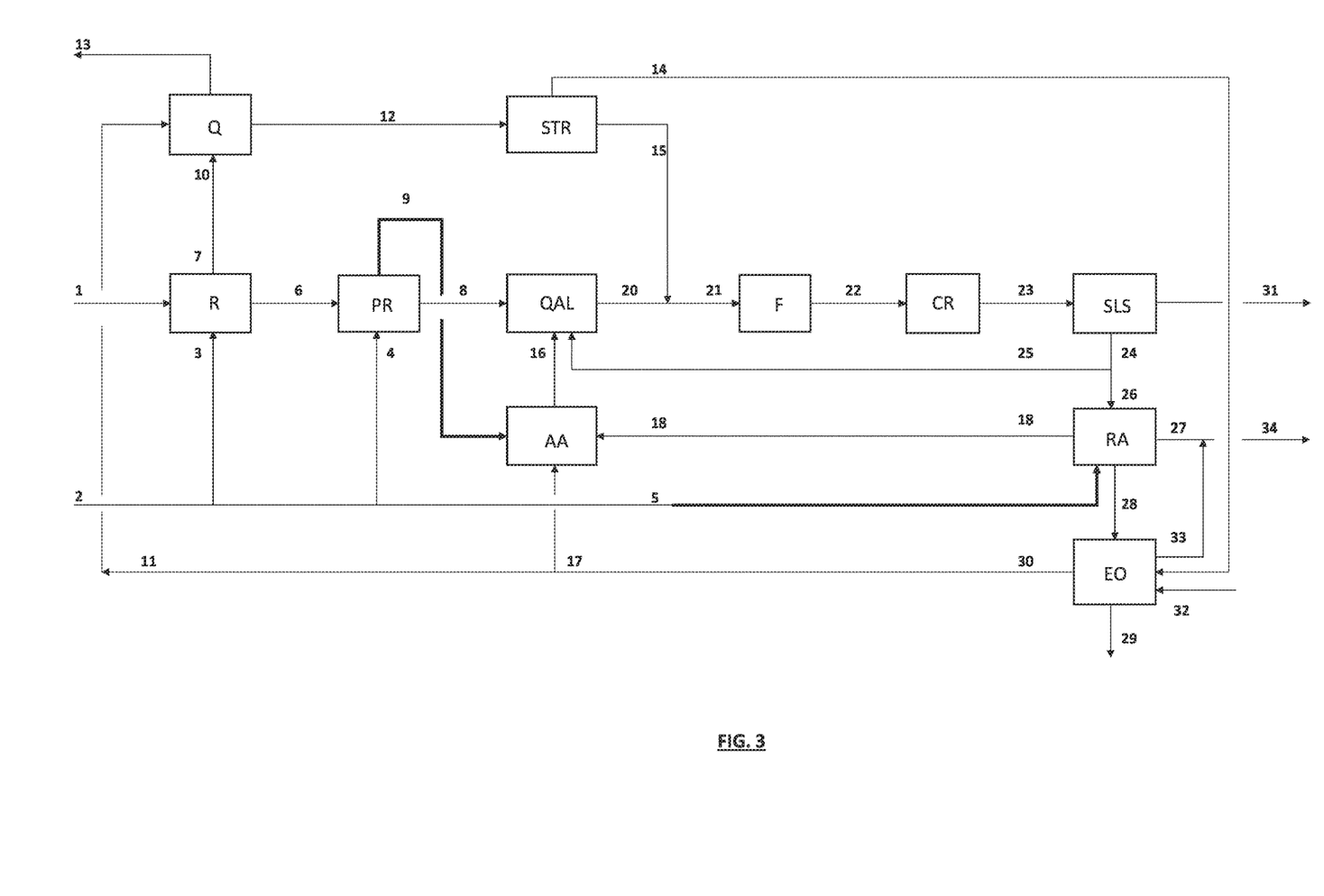
FIG. 3 is a block diagram of a further embodiment of the present invention.
Figure 4:
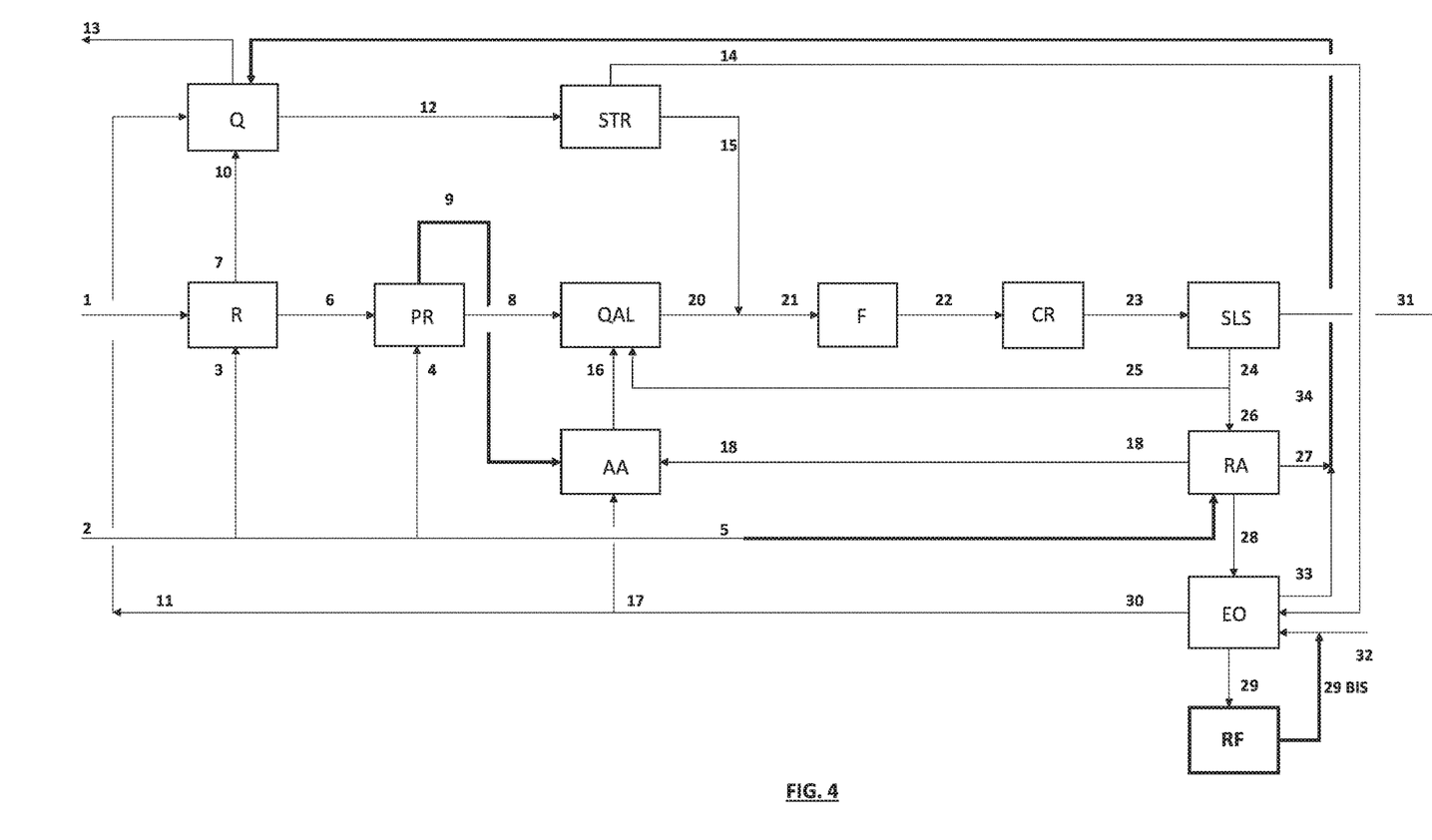
FIG. 4 is a block diagram of yet a further embodiment of the present invention.

The process according to the present invention and the advantages deriving therefrom can be better understood from the following description of a first possible embodiment, illustrated in FIG. 2 and from two further embodiments shown in FIG. 3 and FIG. 4.

In order to facilitate the description and comparison with the prior art, the same abbreviations and numbers as in FIG. 1 representing the state of the art have been retained in FIGS. 2-4.

The block diagram of FIG. 2 shows the main sections of a plant for the production of melamine and the main streams of materials according to a first embodiment of the process of the present invention.

The stream 1 of liquid urea is fed to the reaction section R, at a temperature higher than the melting point (equal to about 133° C.) together with the stream 3 of anhydrous gaseous $NH_3$. The section R comprises a reactor equipped with a suitable heating system, which keeps the reagent system at a temperature of about 360-420° C.; the pressure is maintained at a value higher than 70 $bar_{rel}$.

Inside the reactor R, or in one or more separators positioned downstream (not shown in FIG. 2), the liquid/gas biphasic effluent produced by the pyrolysis reaction of urea is separated into a liquid stream 6 of raw melamine comprising unreacted urea, $NH_3$, $CO_2$ and impurities such as OATs and polycondensates, and a first stream of anhydrous off-gases 7 comprising $NH_3$ and $CO_2$ saturated with melamine vapour. The liquid stream 6 of raw melamine and the stream 7 of anhydrous off-gases are subjected to two different treatments for the recovery of melamine contained therein.

The stream 7 of anhydrous gases is sent to the washing section Q in order to absorb the melamine contained therein bringing it into solution; two streams therefore exit from the section Q, stream 13 of off-gases composed of $NH_3$ and $CO_2$ saturated with water in vapour phase, which leave the melamine production plant and are sent to subsequent treatment at the urea plant, and stream 12, composed of water, $NH_3$, $CO_2$ and melamine in solution, which is fed to the vapour stripping section STR to remove the $CO_2$ from said solution.

The liquid stream 6 of raw melamine is sent to a post-reaction section PR, which preferably operates under the same temperature and pressure conditions as the section R, or at a slightly lower pressure. The post-reaction section PR therefore receives stream 6 of raw melamine and stream 4 of overheated anhydrous gaseous melamine which enters into close contact with the stream 6 of raw melamine. The mass ratio between said stream 4 and said stream 6 ranges from 0.06 to 0.6.

The anhydrous gaseous $NH_3$ stream 4, flows in close contact with the liquid stream of raw melamine 6, extracting the $CO_2$ dissolved therein, increasing the partial pressure of ammonia in proportion to the quantity of ammonia fed. The increase in the partial pressure of ammonia and the permanence of the raw melamine under the conditions of the post-reactor offer advantageous secondary effects:
a) they almost completely advance the conversion of the unreacted urea to melamine, resulting in an increase yield;
b) they advance the conversion of OATs into melamine. The degree of conversion of the OATs into melamine is in relation to the residence time of the stream 6 in contact with the stream 4 having an increased partial pressure of $NH_3$, in the section PR;
c) they favour the reconversion of polycondensates to melamine until the concentration is reduced by about 50%.

A first stream in gas phase composed of $NH_3$ and $CO_2$, saturated with melamine in vapour phase (stream 9) and a second stream in liquid phase (stream 8), composed of partially purified liquid melamine, impoverished in $CO_2$, leave the post-reaction section PR.

From the above it is evident that the greater the amount of ammonia fed to the post reactor, the greater the effect will be of the $CO_2$ removal and the greater the partial pressure of ammonia in the liquid phase inside the post reactor will be, with the above-mentioned benefits. It is also clear however that the greater the amount of $NH_3$ fed (stream 4), the greater the amount will be of anhydrous gases composed of $NH_3$ and $CO_2$ saturated with melamine in vapour phase exiting from the post reactor PR (stream 9).

As previously indicated, according to the state of the art, the melamine which exits in vapour phase with stream 9 is absorbed and solubilized in the subsequent section Q, consequently, the greater the amount of the anhydrous gases of stream 9, the greater will be the amount of wet off-gases produced by Q, which must be treated and reconverted to urea at the urea production plant, and the greater will be the amount of water necessary for solubilizing the melamine contained therein.

As the solution containing melamine (stream 12) is fed to a stripping section STR, there is therefore also another drawback linked to the quantity of ammonia fed to the post-reactor which is the quantity of vapour necessary for effecting the stripping of $CO_2$.

In order to reduce as much as possible the drawbacks linked to the amount of ammonia fed to the post-reactor described above, in the processes according to the state of the art, there is the tendency to feed the minimum possible amount of ammonia sufficient for reaching a satisfactory degree of transformation of the by-products.

In order to remedy these drawbacks, it has been surprisingly found that by treating the gases leaving the post-reaction section PR (stream 9) in the ammonia absorption section AA, i.e. the mixing and heat recovery section, the drawbacks of the state of the art are overcome, obtaining the following advantages:
i) the sensible heat and condensation heat of the gases are completely recovered, obtaining an equal reduction in the heat necessary for heating the ammonia solution (stream 16), to be fed to the quench-ammonolysis section QAL;
ii) all the ammonia fed to the post-reactor PR is completely recovered within the melamine production plant, reducing the make-up ammonia required from the outside in an equal amount (stream 5);
iii) the wet off-gases produced by the process decrease in proportion to the same quantity of anhydrous gases which, in the process according to the state of the art, were sent from the post-reactor PR to the washing section with water Q where they exited saturated with water in stream 13;
iv) the quantity of solution be sent to the stripping section STR is reduced, with a proportional reduction in the vapour necessary.

Furthermore, as the stream 9 of anhydrous gases leaving the post-reaction section is no longer sent to the washing section Q, no longer contributing to the quantity of wet off-gases produced nor giving rise to the other negative effects previously described, the quantity of anhydrous ammonia 4 fed to the section PR can be increased, thus obtaining a greater efficiency of the section, with a higher conversion of polycondensates into melamine and with the almost complete transformation of OATs into melamine.

As there are fewer polycondensates, this also allows a reduction in the temperature and residence time in the purification section, with a reduction in the hydrolysis phenomena of melamine to form OATs, thus reducing the volume of the equipment and consequently also the investment costs.

A liquid stream of melamine therefore leaves the section PR (stream 8) which is not only practically free of $CO_2$, but is also partially purified, as it is practically free of urea and does not contain or contains quantities further reduced in OATs and polycondensates.

As indicated above, stream 7 of anhydrous gases leaving the section R is sent to the washing section Q for absorbing the melamine contained therein, bringing it in solution; this melamine is recovered in the section Q by putting stream 7 in contact with an aqueous washing stream, preferably consisting of one or more streams taken from suitable points of the melamine plant (in FIG. 2, these streams are represented by a single stream 11), with the formation of an aqueous stream (stream 12) comprising melamine, $NH_3$ and $CO_2$. The section Q operates at temperatures within the range of 125-190° C., preferably 160-175° C., and at pressures ranging from 20 to 30 $bar_{rel}$, preferably about 25 $bar_{rel}$; the mass ratio between stream 11 and stream 7 ranges from 0.3 to 2.0, preferably from 0.4 to 0.7.

The gaseous stream leaving section Q after the washing (stream 13) consists of wet off-gases substantially comprising $NH_3$, $CO_2$ and the saturation water vapour; it is sent to the urea plant as such or after being subjected to treatment (not indicated in FIG. 2) such as condensation by absorption in aqueous solution.

The aqueous stream leaving the section Q (stream 12) is sent to a section STR for the separation of $CO_2$, where a part of the $CO_2$ contained therein is removed by stripping with vapour, produced for example by a reboiler at the bottom of the stripper itself. A gaseous stream rich in $CO_2$ (stream 14) is recovered from the section STR and is sent to a point of the process where it can no long contribute to lowering the pH in crystallization, together with an aqueous stream comprising melamine, $NH_3$ and impoverished in $CO_2$ (stream 15).

As already indicated, the liquid stream 8 of melamine, impoverished in $CO_2$ and partially purified, also leaves the post-reaction section PR. It is sent, as shown in FIG. 2, to a quench-ammonolysis section QAL, wherein the quench (dissolution in water of raw melamine) and ammonolysis (elimination of the polycondensates) treatment takes place. On the basis of what is indicated above, the solution according to the present invention allows this section to be resized as the almost complete transformation of OATs and polycondensates already takes place in the PR, thanks to the increased quantity of $NH_3$ fed.

The section QAL can be composed of one or more stationary apparatuses, preferably a single piece of equipment. The stream 8 enters the bottom of this equipment, maintained under vigorous stirring, and is put in close contact with an aqueous ammonia solution (stream 16), in which it is completely dissolved at a temperature of 160-180° C., preferably 165-172° C., even more preferably 165-168° C.

The aqueous ammonia solution 16 comes from the ammonia absorption section AA, to which an aqueous stream (stream 17) coming from the subsequent steps of the melamine process, is fed together with stream 9 in gas phase composed of $NH_3$ and $CO_2$ saturated with melamine in vapour phase coming from the section PR and a stream (19) obtained by combining the stream of $NH_3$ preferably gaseous (18), also coming from the subsequent steps of the melamine process and the liquid make-up stream of $NH_3$ 5; a direct recycling aqueous stream of crystallization mother liquor (stream 25) is also sent to the quench-ammonolysis section.

At the inlet of the quench-ammonolysis section, the mass ratios between the combination of streams 16 and 25 and the molten melamine stream 8 are selected so as to have concentrations of $NH_3$ at the outlet ranging from 10% to 17% by mass (preferably from 12% to 15% by mass) in the aqueous ammonia solution comprising purified melamine (stream 20).

The residence time in the quench-ammonolysis equipment is sufficient for almost completely eliminating the possible residual polycondensates present in stream 8, mainly transforming them into melamine.

Stream 15 coming from section STR is preferably joined with stream 20 coming from the quench-ammonolysis section to form stream 21; from here on, the melamine that left the reaction R and post-reaction PR sections in vapour phase, joins the melamine which left the same sections in liquid phase, and is subjected to the same treatment.

The stream 21 is sent to the filtration section F, composed of finisher filters which also complete the ammonolysis treatment. The stream leaving the section F (stream 22) is sent to the crystallization section Cr, where the melamine is crystallized by decreasing the temperature to a value of about 40-50° C., obtaining an aqueous suspension of high-purity melamine (stream 23).

The low content of $CO_2$ in stream 15, obtained through the section STR, allows the pH in crystallization to be kept at a high value, thus being able to operate under less favourable conditions for the precipitation of OATs. These advantageous conditions for the crystallization of pure melamine are obtained in the section STR, by separating the $CO_2$ from the melamine stream recovered from the off-gases (stream 12). The stream 23 leaving the section Cr is subjected to a solid/liquid separation in the section SLS, where the melamine crystals (stream 31) are separated from the crystallization mother liquor (stream 24) and sent to the drying and packaging sections (not shown in FIG. 2). The stream 24 leaving the separator SLS is divided into two streams (streams 25 and 26): stream 25 is recycled directly to the quench-ammonolysis section QAL, whereas stream 26 is sent to the ammonia recovery section RA.

The fraction of mother liquor not directly recycled (stream 26) is subjected to deammoniation in the section RA, which separates three streams: a stream of $NH_3$ substantially free of $CO_2$, to be recycled to the ammonolysis section QAL (stream 18); a stream rich in $CO_2$ and ammonia (stream 27); an aqueous stream comprising melamine, OATs and substantially free of $CO_2$ and $NH_3$ (stream 28).

The stream of $NH_3$ 18 is extracted from the section RA, preferably in the gaseous state, combined with the liquid make-up stream of $NH_3$ 5, thus forming stream 19, and then mixed in the ammonia absorption section (AA) with a part of the aqueous stream 17, coming from the subsequent phases of the melamine process and with stream 9 in gas phase, saturated with melamine in vapour phase and mainly composed of $NH_3$ and $CO_2$ coming from PR; in this mixing and heat recovery section AA, the aqueous ammonia solution 16 is formed, in which the melamine contained in the stream of anhydrous gas 9 is dissolved, and both the sensible heat and the condensation heat of the gases is recovered; in particular, the condensation enthalpy of $NH_3$ also serves for heating the resulting stream 16, with a positive effect on the thermal balance of the section QAL and therefore on the vapour consumption of the whole plant.

The stream 27 leaving the section RA and containing $CO_2$, ammonia and water, is combined with stream 33 containing $H_2O$, $CO_2$ and $NH_3$ coming from the section EO to form stream 34, normally called side-stream, which is sent directly to the urea plant, thus eliminating $CO_2$ from the plant, but also eliminating the ammonia contained in the solution which forms stream 34. This ammonia must be reintegrated by reintegration or make-up (stream 5). The melamine plant therefore requires a total amount of ammonia equal to the sum of streams 3-4-5 (stream 2).

The stream of deammoniated mother liquor 28 is sent to a section EO for the elimination of the OATs and to obtain an aqueous solution (stream 30) to be recycled to the ammonia absorption section AA (stream 17) and off-gas washing section Q (stream 11).

In the section EO, the whole stream 28 is sent for decomposition in order to recover the organic compounds in the form of $CO_2$ and $NH_3$, obtaining a stream of water (stream 29) substantially without impurities, which can be discharged or reused in a suitable point of the plant, and a stream of water 30 to be recycled to the sections QAL and Q (streams 17 and 11) and a stream 33 containing $H_2O$, $CO_2$ and $NH_3$ which is joined with stream 27 coming from the section RA, forming stream 34. The section EO also receives the make-up or reintegration water (stream 32) in order to reintegrate the water outlets with off-gases (stream 13), side stream (stream 34) and with the stream of water 29 if discharged and not recycled to the plant.

A second embodiment of the process according to the present invention is schematically represented in FIG. 3. The block diagram of FIG. 3 shows the main sections of a plant for the production of melamine and the main streams of materials in accordance with a second embodiment of the process according to the present invention of which only the different aspects with respect to the first embodiment shown in FIG. 2 will be described hereunder.

In the embodiment represented in FIG. 3, the make-up ammonia 5 is fed as reflux ammonia to the section RA, thus reducing the consumption of cooling water for the condensation of the part of ammonia vapour, leaving the head of the section RA, necessary for the internal reflux of said section.

The stream of $NH_3$ 18 is extracted from the section RA, preferably in the gaseous state, and sent to the ammonia absorption section (AA) where it is mixed with a part of the aqueous stream 17, coming from the subsequent steps of the melamine process and with stream 9 in gas phase, saturated with melamine in vapour phase, mainly composed of $NH_3$ and $CO_2$ coming from PR.

The indication of stream 19 is not present in FIG. 3 as stream 18 is fed to the section AA directly from the section RA, whereas the make-up ammonia 5 is sent directly to the section RA.

In addition to the advantages already indicated for the embodiment of FIG. 2, the solution represented in FIG. 3 therefore allows a reduction in the quantity of cooling water necessary for the condensation of part of the ammonia vapour, leaving the head of the section RA, necessary for the internal reflux of said section, with a consequent further energy advantage, at the same time avoiding the mixing of liquid ammonia and gaseous ammonia.

In the embodiment represented in FIG. 4, in addition to what has already been described for the embodiment of FIG. 3, the stream 34 containing $CO_2$, ammonia and water, normally called side stream, is sent to the washing section Q of anhydrous off-gases.

In this way, the total amount of $H_2O$ leaving the melamine plant with the off-gases (stream 13) and with the side stream (stream 34) is reduced when these are discharged separately.

The stream of water (stream 29) substantially free of impurities, coming from the section EO, can be sent to a section RF i.e. a cooling section, where it is cooled to be used as make-up water.

It leaves the section RF as stream 29bis, is combined with the make-up or reintegration water (stream 32), fed to EO for reintegrating the outlets of water with the off-gases (stream 13) and to obtain a plant for the production of melamine completely free of liquid discharges.

Example 1 (Comparative)

In a melamine plant having a nominal capacity of 40,000 t/y (5,000 t/h), according to the state of the art represented in FIG. 1 of patent EP2385043, 16.0 t/h of molten urea and 1.0 t/h of gaseous $NH_3$ (stream 3) were sent to the reaction section R. The reactor operated at 380° C. and 80 $bar_{rel}$.

11.8 t/h of anhydrous off-gases (stream 7) comprising melamine vapour and 5.2 t/f of liquid raw melamine (stream 6) were separated from the reactor.

This liquid melamine was treated in the section PR with 1.1 t/h of anhydrous gaseous $NH_3$ (stream 4), under the same conditions as the reaction section R, obtaining 5.1 t/h of liquid melamine (stream 8) and 1.2 t/h of anhydrous off-gases (stream 9) comprising melamine vapour which, combined with the off-gases leaving the section R, formed stream 10 of 13.0 t/h, comprising 3.8% by mass of melamine vapour.

Stream 8 of liquid melamine leaving the bottom of the section PR was sent to the quench-ammonolysis section QAL, where the quench (dissolution in water of the raw melamine) and the ammonolysis (elimination of the polycondensates) treatments were effected.

More specifically, stream 8 was kept under vigorous stirring and was put in close contact with an aqueous ammonia solution (stream 16) in which it was completely dissolved at a temperature of 172° C. and a pressure of 25 $bar_{rel}$.

More specifically, the aqueous stream 16 was obtained by combining an aqueous stream (stream 17) coming from the section EO and a stream of $NH_3$ (stream 19), in turn formed by combining the stream of $NH_3$ (stream 18) coming from the section RA and the make-up stream of $NH_3$ (stream 5): stream 5 fed proved to be equal to 1.9 t/h.

A direct recycling aqueous stream of the crystallization mother liquor (stream 25) was also sent to the quench-ammonolysis section QAL.

The melamine plant was then fed with a quantity of ammonia equal to the sum of streams 3-4-5, equal to 4-0 t/h (stream 2).

The mass ratios between the combination of streams 16 and 25 and the stream of molten melamine, stream 8, at the inlet of the quench-ammonolysis section QAL, were selected so as to have concentrations of $NH_3$ at the outlet, equal to about 14% by mass in the aqueous ammonia solution comprising purified melamine (stream 20).

In the quench-ammonolysis equipment, the operating conditions indicated and the residence time were such as to almost completely eliminate the polycondensates present in stream 8, largely transforming them into melamine.

The gaseous stream 10, obtained by joining the anhydrous streams of off-gases from the reactor and from the stripper (stream 9), was sent to a washing section Q which operated at 169° C. and 25 bar$_{rel.}$, where it was put in contact in countercurrent with 7.0 t/h of a recycled aqueous solution (stream 11).

The washed off-gases leaving the head of the washing column (stream 13), containing 18% by mass of water and substantially free of melamine, were sent to the adjacent urea plant to recover the $NH_3$ and $CO_2$ contained therein.

6.4 t/h of an aqueous solution (stream 12) comprising 0.5 t/h of melamine entering as vapour with the off-gases, and 4.5% by mass of $CO_2$, left the bottom of the washing column. This stream was sent to a vapour stripping column, which operates at the bottom at 160° C. and 7 bar$_{rel.}$ 4.6 t/h of an aqueous solution (stream 15) left the bottom of the stripping column where the $CO_2$ was reduced to 0.2% by mass.

This solution (stream 15) was joined with the solution leaving the quench-ammonolysis section (stream 20) and the whole mixture was sent to the filters from which a solution was discharged (stream 22) with less than 100 ppm by mass of polycondensates; this latter solution (stream 22) was then sent to the crystallizer, which operates at a temperature of 45° C. and a pressure of 0.5 bar$_{rel.}$, with a concentration of $CO_2$ of about 0.15% by mass and a pH of about 11.5.

The suspension (stream 23) leaving the crystallizer was sent to a solid/liquid separator (centrifuge), which separated the crystallization mother liquor (stream 24) from the high-purity melamine (titer of over 99.9% by mass with respect to the dry material).

The amount of about 62.6 t/h of mother liquor (stream 24) was divided into two streams. One stream of 7.5 t/h (stream 25) was recycled directly to the quench-ammonolysis section without being subjected to any treatment; the remaining 55.1 t/h (stream 26) was sent to the deammoniation section to recover the $NH_3$ dissolved therein.

The deammoniation section (RA) consists of a distillation column from whose head gaseous, almost anhydrous $NH_3$ exits.

A liquid stream of $CO_2$, $NH_3$ and water, which was recycled in a suitable point of the process, exits from an intermediate plate of the column.

The aqueous solution leaving the bottom of the column (stream 28) was sent to treatment for the elimination of the OATs by thermal decomposition alone. An aqueous solution (stream 30) was thus separated, which was recycled to the quench-ammonolysis (stream 17) and off-gas washing (stream 11), together with another aqueous stream (which can be discharged or reused as water for utilities, for example make-up water at the cooling towers or as process water).

A part of the solution recycled to the quench-ammonolysis section (stream 17) was mixed with the gaseous $NH_3$ leaving the head of the distillation column of the deammoniation section (stream 19), condensing it and recovering the condensation heat.

The consumptions of urea, ammonia and vapour of the whole process according to the state of the art represented in FIG. 1 and object of the present comparative example 1, proved to be equal to 3.2 t/t, 0.80 t/t and 4.3 t/t respectively of melamine produced.

Example 2

A synthesis process of melamine was carried out according to the present invention in the embodiment described in FIG. 2, in a melamine plant having a nominal capacity of 40,000 t/y (5,000 t/h), wherein the gases leaving the post-reaction section PR (stream 9) were treated in the mixing and heat recovery section AA.

The subsequent steps of the process were carried out as indicated in comparative example 1.

The treatment of stream 9 in the section AA had, as first effect, a reduction in the flow-rate of the make-up ammonia (stream 5). In order to keep the concentration of ammonia constant in stream 20 leaving the quench-ammonolysis section QAL, stream 5 of make-up ammonia was in fact reduced.

More specifically, the stream of make-up ammonia 5 was reduced by an amount equal to the ammonia contained in stream 9, i.e. by a quantity equal to 1.1 t/h which is equal to the ammonia fed to the section PR (stream 4). The quantity of make-up ammonia therefore proved to be lower than that necessary according to comparative example 1 (1.9 t/h).

The total amount of $NH_3$ which must be fed to the melamine plant therefore proved to be equal to the sum of streams 3-4-5 (stream 2), i.e. equal to the sum of 1.0 t/h, 1.1 t/h and 0.8 t/h.

Stream 2 of ammonia fed to the melamine plant is therefore equal to 2.9 t/h which correspond to 0.58 t/t of melamine produced.

The total quantity of ammonia therefore also proved to be lower than the amount necessary according to comparative example 1 (4.0 t/h).

Furthermore, as stream 9 of anhydrous gases leaving the post-reaction section is no longer sent to the washing section Q, it no longer contributes to the quantity of wet off-gases produced, neither does it give rise to the other negative effects described above, and this allowed the quantity of anhydrous ammonia (stream 4) fed to the section PR, to be increased, thus obtaining a higher efficiency of the section, with a higher conversion of polycondensates into melamine and with the almost complete transformation of OATs into melamine.

A further advantage of the process according to the present example which provides for the treatment of stream 9 in the section AA described above, is the complete recovery of the sensible heat and condensation heat of the gases, obtaining an equal reduction in the heat necessary for heating the ammonia solution (stream 16), to be fed to the quench-ammonolysis section QAL.

The heat recovered in treating stream 9 in the section AA allowed a reduction equal to 450 kg/h in the quantity of saturated vapour used for heating the ammonia solution (stream 16), with respect to the process according to comparative example 1.

The ammonia and vapour consumptions of the process in accordance with the present invention according to the embodiment of FIG. 2, proved to be equal to 0.58 t/t and 4.21 t/t respectively of melamine produced, against the corresponding values of 0.80 t/t and 4.3 t/t of melamine produced of the process according to comparative example 1.

Example 3

A synthesis process according to the present invention in the embodiment described in FIG. 3, was carried out in a melamine plant having a nominal capacity of 40,000 t/y (5,000 t/h), the make-up ammonia (stream 5) was fed as reflux ammonia to the section RA, thus reducing the consumption of cooling water for the condensation of the part of ammonia vapour leaving the head of the section RA, necessary for the internal reflux of said section.

The other steps of the process were carried out as indicated in the previous example 2.

In addition to the reduction in the consumption of ammonia indicated in example 2 and the heat recovered in treating stream 9 in the section AA, which allowed a reduction of 450 kg/h in the quantity of saturated vapour used for heating the ammonia solution (stream 16) according to example 2, the embodiment of the present example led to a reduction in the consumption of cooling water, with a temperature differential of 9° C., of 20 m³/h for a melamine plant having a nominal capacity of 40,000 t/y (5,000 t/h).

Example 4

A synthesis process according to the present invention in the embodiment described in FIG. 4, was carried out in a melamine plant having a nominal capacity of 40,000 t/y (5,000 t/h), stream 34 containing $CO_2$, ammonia and water, normally called side-stream, was recycled within the melamine plant to the washing section of anhydrous off-gases Q, instead of being sent to the urea plant.

In this way, the total quantity of $H_2O$ leaving the melamine plant with the off-gases (stream 13) and with the side stream (stream 34), when these are discharged separately, was reduced.

The other steps of the process were carried out as indicated in the previous example 3.

By recycling stream 34 to the washing section of anhydrous off-gases Q, its water content was internally recovered at the melamine plant in stream 12, whereas the content of $NH_3$ and $CO_2$ was recycled to the urea plant with stream 13, containing all the off-gases generated in the reaction section R and in the post-reaction section PR and a water content of 18% by weight, corresponding to 2.75 t/h.

The stream of water (stream 29) substantially free of impurities, coming from the section EO, was sent to the cooling section RF, where it was cooled to be used as make-up water.

When stream 34 was entirely recycled within the melamine plant, together with said stream 29, the water content which had to be reintegrated at the melamine plant with stream 32, proved to be equal to the water content of the stream of off-gases 13.

In addition to the reduction in the consumption of ammonia, indicated in example 2, the heat recovered in treating stream 9 in the section AA, which allowed a reduction equal to 450 kg/h of the quantity of saturated vapour used for heating the ammonia solution (stream 16) again according to example 2, a reduction in the consumption of cooling water, with a differential of temperature of 9° C., of 20 m³/h for a melamine plant having a nominal capacity of 40,000 t/y (5,000 t/h), according to example 3, the embodiment of the present example allowed a reduction in the flow-rate of stream 32 by an amount equal to the quantity of water contained in stream 34 (1.6 t/h) and the quantity of water contained in stream 29 (11 t/h), obtaining a plant for the production of melamine completely free of liquid discharges.

The invention claimed is:

1. A process for the production of melamine by the pyrolysis of urea comprising the following steps:
    a) producing melamine by the pyrolysis of urea in a specific reactor (R) and separating a biphasic liquid/gas effluent produced in the pyrolysis reaction of urea into a liquid stream of raw melamine and into a first stream of anhydrous off-gases comprising NH3, CO2 and melamine vapour;
    b) putting said liquid stream of raw melamine in contact with a stream of anhydrous gaseous NH3 in a specific post-reactor (PR) and forming a liquid stream of melamine impoverished in CO2 and partially purified and a second stream of anhydrous gases comprising NH3, CO2 and melamine vapour;
    c) putting the first stream of anhydrous gases coming from step a) in contact with at least one aqueous washing stream, forming an aqueous stream, comprising melamine, NH3, CO2 and a gaseous stream of wet off-gases, comprising NH3, CO2 and water vapour;
    d) mixing the second stream of anhydrous gases coming from step b) with a stream of recycled water and forming an aqueous ammonia solution in which the melamine contained in the stream of anhydrous gases is dissolved, recovering the sensible heat and condensation heat of the gases;
    e) removing, from the aqueous stream of step c), comprising melamine, NH3, CO2, at least a part of the CO2 contained therein and forming a gaseous stream comprising the CO2 removed and an aqueous stream comprising melamine, NH3 and impoverished in CO2;
    f) subjecting the liquid stream of melamine impoverished in CO2 and partially purified, coming from the post-reactor, to a quench-ammonolysis treatment by contact with the aqueous ammonia solution obtained in step d), and the formation of an aqueous ammonia stream comprising purified melamine;
    g) recovering the melamine contained in the aqueous ammonia stream comprising purified melamine coming from step f) and the melamine contained in said aqueous stream comprising melamine and impoverished in CO2 coming from step (e) by means of a crystallization step by cooling and separation, with the formation of a stream of crystallized melamine and a stream of mother liquor.

2. The process according to claim 1, wherein, in step d), the second stream of anhydrous gases coming from step b) is mixed with the stream of recycled water and with a stream obtained by joining a make-up ammonia stream and a stream of recycled ammonia forming the aqueous ammonia solution.

3. The process according to claim 1, comprising feeding a make-up ammonia stream to a subsequent deammoniation treatment of the portion of mother liquor stream not directly recycled, stream.

4. The process according to claim 1, characterized in that at least a part of said mother liquor stream obtained in step g) is used as aqueous stream in the quench-ammonolysis treatment of said liquid melamine stream impoverished in CO2 and partially purified.

5. The process according to claim 3, characterized in that at least a part of said mother liquor stream obtained in step g) is subjected to deammoniation treatment, with the formation of a gaseous stream of NH3 substantially free of CO2, a stream comprising CO2 and an aqueous stream of deammoniated mother liquor.

6. The process according to claim 5, characterized in that said stream comprising CO2, ammonia and water is joined with a further stream, containing H2O, CO2 and NH3 and coming from a following step of decomposition of the stream to form a single stream and recycled to a production plant of urea directly or after treatment which reduces its water content or said stream containing CO2, ammonia and water, is sent to the washing step c) of the anhydrous off-gases.

7. The process according to claim 5, characterized in that said aqueous stream of deammoniated mother liquor is subjected to a decomposition treatment with the recovery of NH3 and CO2, and the production of an aqueous stream which is partly recycled as aqueous washing stream to said step c) and partly recycled as aqueous stream to contribute to forming said aqueous ammonia stream fed to step f) for the quench-ammonolysis treatment and a stream containing H2O, CO2 and NH3 that is joined with the stream comprising CO2, ammonia and water, coming from the deammoniation treatment.

8. The process according to claim 5, characterized in that said gaseous stream of NH3 substantially free of CO2, coming from the deammoniation treatment, is mixed with a part of said aqueous stream, to recover its condensation heat in step d).

9. The process according to claim 1, characterized in that said aqueous stream comprising melamine, NH3 and impoverished in CO2 coming from step e), is joined with said aqueous ammonia stream comprising purified melamine, with the formation of a single stream to be subjected to said step g).

10. The process according to claim 1, characterized in that in step e), the removal of CO2 from said aqueous stream comprising melamine, NH3 and CO2 is effected by depressurization or by means of stripping.

11. The process according to claim 1, characterized in that said stream comprising removed CO2, obtained in step e), is recycled in a step of the same process following said step g) for the recovery of melamine through crystallization by cooling and separation.

12. The process according to claim 1, characterized in that said stream of wet off-gases, coming from step c), comprising NH3, CO2 and water vapour, is recycled to a plant for the production of urea, as such or after being subjected to a condensation treatment by absorption in aqueous solution or another type of treatment.

13. The process according to claim 5, characterized in that said aqueous stream of deammoniated mother liquor is separated into:
   i) an aqueous stream enriched in melamine which is partly recycled as aqueous washing stream to said step c) and partly recycled as aqueous stream to contribute to forming said aqueous ammonia stream fed to step f) for the quench-ammonolysis treatment;
   ii) an aqueous stream enriched in OATs, suitable for being decomposed with the recovery of NH3 and CO2.

14. A plant for the implementation of a process for the production of melamine by the pyrolysis of urea according to claim 1, comprising:
   i) a separation section for separating a biphasic liquid/gas effluent produced in a pyrolysis reaction of urea into a liquid stream of raw melamine and a first stream of anhydrous off-gases comprising NH3, CO2 and melamine steam, said separation section being connected to a reaction section (R) for the pyrolysis of urea from which it receives said biphasic liquid/gas effluent, said separation section being inside or outside said reaction section (R);
   ii) a stripping section or post-reactor (PR) for putting said liquid stream of raw melamine coming from said reaction section (R) in contact with a stream of anhydrous gaseous NH3 and forming a liquid stream of melamine impoverished in CO2 and partially purified and a second stream of anhydrous gases comprising NH3, CO2 and melamine steam, said stripping section (PR) being connected to said reaction section (R) from which it receives said liquid stream of raw melamine;
   iii) a washing section (Q) for putting said first stream of anhydrous off-gases in contact with an aqueous washing stream and forming an aqueous stream comprising melamine, NH3, CO2 and a stream of wet off-gases comprising NH3, CO2 and water vapour, said washing section (Q) being connected to said separation section from which it receives said first stream of anhydrous off-gases;
   iv) a removal section of the CO2 (STR) for removing from said aqueous stream comprising melamine, NH3, CO2, at least a part of the CO2 contained therein and comprising the CO2 removed and an aqueous stream, comprising melamine, NH3 and impoverished in CO2, said removal section of the CO2 (STR) being connected to said washing section (Q) from which it receives said aqueous stream, comprising melamine, NH3, CO2;
   v) a mixing and heat recovery section (AA) for mixing said second stream of anhydrous gases with a stream of recycled water and forming an aqueous ammonia solution in which the melamine contained in the stream of anhydrous off-gases is dissolved, and for recovering both the sensible heat and the condensation heat of the gases, by absorption of the ammonia, said mixing and heat recovery section (AA) being connected to the stripping section or post-reactor (PR) from which it receives said second stream of anhydrous gases and said quench-ammonolysis section (QAL) to which the aqueous ammonia solution is fed;
   vi) a quench-ammonolysis section (QAL) for subjecting the liquid stream of melamine impoverished in CO2 and partially purified, coming from the post-reactor (PR), to a quench-ammonolysis treatment by contact with the aqueous ammonia solution coming from the mixing and heat recovery section (AA), and forming an aqueous ammonia stream, comprising purified melamine, said quench-ammonolysis section (QAL) being connected to said stripping section or post-reactor (PR) from which it receives said liquid stream of melamine impoverished in CO2 and partially purified;
   vii) at least one recovery section of the melamine (CR, SLS) for recovering both the melamine contained in said aqueous ammonia stream comprising purified melamine and also the melamine contained in said aqueous stream comprising melamine, NH3 and impoverished in CO2 through crystallization by cooling and separation, with the formation of a stream of crystallized melamine and a stream of mother liquor, said recovery section of the melamine (CR, SLS) being connected to both said quench-ammonolysis section (QAL) from which it receives the aqueous ammonia stream comprising purified melamine and to said removal section of the CO2 (STR) from which it receives said aqueous stream comprising melamine, NH3 and impoverished in CO2.

15. The process according to claim 4, characterized in that at least a part of said mother liquor stream obtained in step g) is subjected to deammoniation treatment, with the formation of a gaseous stream of NH3 substantially free of CO2, a stream comprising CO2 and an aqueous stream of deammoniated mother liquor.

16. The process according to claim 15, characterized in that said stream comprising CO2, ammonia and water is joined with a further stream, containing H2O, CO2 and NH3 and coming from a following step of decomposition of the stream to form a single stream and recycled to a production plant of urea directly or after treatment which reduces its water content or said stream containing CO2, ammonia and water, is sent to the washing step c) of the anhydrous off-gases.

17. The process according to claim 15, characterized in that said aqueous stream of deammoniated mother liquor is subjected to a decomposition treatment with the recovery of NH3 and CO2, and the production of an aqueous stream which is partly recycled as aqueous washing stream to said step c) and partly recycled as aqueous stream to contribute to forming said aqueous ammonia stream fed to step f) for the quench-ammonolysis treatment and a stream containing H2O, CO2 and NH3 that is joined with the stream comprising CO2, ammonia and water, coming from the deammoniation treatment.

18. The process according to claim 15, characterized in that said gaseous stream (18, 19) of NH3 substantially free of CO2, coming from the deammoniation treatment, is mixed with a part of said aqueous stream, to recover its condensation heat in step d).

19. The process according to claim 15, characterized in that said aqueous stream of deammoniated mother liquor is separated into:

i) an aqueous stream enriched in melamine which is partly recycled as aqueous washing stream to said step c) and partly recycled as aqueous stream to contribute to forming said aqueous ammonia stream fed to step f) for the quench-ammonolysis treatment;

ii) an aqueous stream enriched in OATs, suitable for being decomposed with the recovery of NH3 and CO2.

* * * * *